(12) United States Patent
Hossain

(10) Patent No.: US 6,683,205 B2
(45) Date of Patent: Jan. 27, 2004

(54) SYNTHESIS OF 2-ARYL PROPENOIC ACID ESTERS FOR THE PRODUCTION OF NON-STEROIDAL ANTI-INFLAMMATORY DRUGS

(75) Inventor: M. Mahmun Hossain, Glendale, WI (US)

(73) Assignee: WISYS Technology Foundation, Inc., Madison, WI (US)

( * ) Notice: Subject to any disclaimer, the term of this patent is extended or adjusted under 35 U.S.C. 154(b) by 292 days.

(21) Appl. No.: 09/784,639

(22) Filed: Feb. 15, 2001

(65) Prior Publication Data

US 2002/0120153 A1 Aug. 29, 2002

(51) Int. Cl.$^7$ ............................................... C07C 51/36
(52) U.S. Cl. ..................................................... 562/460
(58) Field of Search ........................................ 562/466

(56) References Cited

U.S. PATENT DOCUMENTS 5,198,561 A 3/1993 Chan et al.

OTHER PUBLICATIONS

Holmquist J Org Chem 54 3258 1989.*
Harrington, P. J. and Lodewijk, Eric, "Twenty Years of Naproxen Technology", *Organic Process Research & Development*, 1, 72–76 (1997).
Hiyama, T. et al., "A Facile, Practical Synthesis of 2–(6–Methoxy–2–naphthyl)propenoic Acid", *Bulletin Chemical Society of Japan*, vol. 63, No. 2, 640–642 (1990).
Mahmood, S. and Hossain, M., "Iron Lewis Acid Catalyzed Reactions of Aromatic Aldehydes with Ethyl Diazoacetate: Unprecedented Formation of 3–Hydroxy–2–arylacrylic Acid Ethyl Esters by a Unique 1,2–Aryl Shift", *The Journal of Organic Chemistry*, vol. 63, No. 10, 3333–3336 (1998).
Ohta, T., "Asymmetric Hydrogenation of Unsaturated Carboxylic Acids Catalyzed by BINAP–Ruthenium(II) Complexes", *The Journal of Organic Chemistry*, vol. 52, 3174–3176 (1987).
Quallich, G. and Woodall, T., "In Situ Oxazaborolidines, Practical Enantioselective Hydride Reagents", *Synlett*, 929–930 (Dec. 1993).
Scrivanti, A. and Matteoli, U., "A Convenient Synthesis of 2–(6–Methoxy–2–naphthyl)propenoic Acid (a Naproxen Precursor)", *Tetrahedron Letters*, vol. 36, No. 49, 9015–9018 (1995).

* cited by examiner

Primary Examiner—Robert Gerstl
(74) Attorney, Agent, or Firm—Michael Best & Friedrich, LLP

(57) ABSTRACT

A method of producing a compound of the formula:

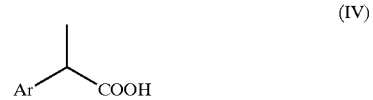

(IV)

and its pharmaceutically acceptable salts, wherein Ar is a substituted or unsubstituted aromatic or heteroaromatic group; comprising:

(1) reacting a compound of the formula:

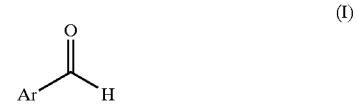

(I)

wherein Ar is as described above, with $N_2CHCOOR$, wherein R is alkyl, in the presence of a catalytic amount of a Bronsted acid or Lewis acid to form a compound of the formula:

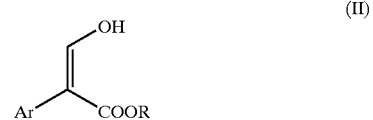

(II)

wherein Ar and R are as described above; and (2) reacting the compound of formula (II) with a reducing agent in the presence of an alkyl amine to form a compound of the formula:

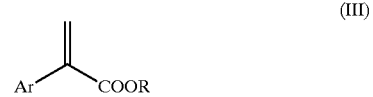

(III)

wherein Ar and R are as described above.

36 Claims, No Drawings

US 6,683,205 B2

SYNTHESIS OF 2-ARYL PROPENOIC ACID ESTERS FOR THE PRODUCTION OF NON-STEROIDAL ANTI-INFLAMMATORY DRUGS

This invention was made with United States government support awarded by the following agencies: NIH GM/00 51063. The United States has certain rights in this invention.

FIELD OF THE INVENTION

The present invention relates to the synthesis of non-steroidal anti-inflammatory drugs ("NSAIDs"). More particularly, the invention relates to the synthesis of 2-aryl-3-hydroxy-propenoic acid esters and 2-aryl propenoic acid esters, which are key intermediates in the production of certain NSAIDs and their pharmaceutically acceptable salts.

BACKGROUND OF THE INVENTION

Efficient practical routes to pharmaceutically-active compounds are in great demand. Manufacturers constantly seek synthetic routes that are environmentally friendly with respect to solvent volume, purity, yield and waste reduction. In addition, the cost of manufacturing drugs generally decreases as the number of steps in the synthetic route decreases. This is particularly true with respect to (S)-2-(6-methoxy-2-naphthyl)propanoic acid, which is also known as naproxen.

Naproxen is one of the most potent NSAIDs currently available, and as a result is extremely popular with consumers, generating sales of over one billion dollars annually.

Unfortunately, naproxen is difficult to synthesize in an efficient and environmentally friendly manner. Since naproxen is the optically active (S) form of 2-(6-methoxy-2-naphthyl)propanoic acid, and is presently marketed in a composition free of the (R) stereoisomer, it has been proposed to produce naproxen using a catalytic asymmetric hydrogenation process.

Specifically, it has been proposed to synthesize naproxen from 2-(6-methoxy-2-naphthyl)propenoic acid in a catalytic asymmetric hydrogenation reaction using a ruthenium (S)-BINAP catalyst or a tol-BINAP-based catalyst. This synthesis route is generally shown in FIG. 1 below.

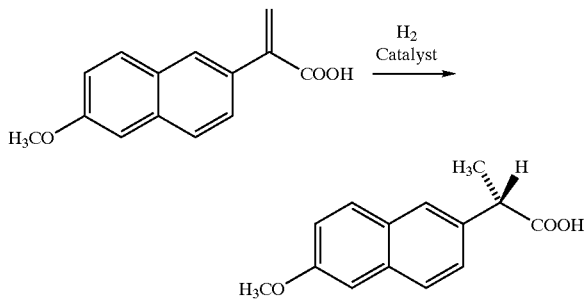

While this is an extremely efficient and effective process, it has not been utilized to date on a commercial scale due to the difficulty and high cost involved in producing the 2-(6-methoxy-2-naphthyl)propenoic acid precursor compound. Therefore, an efficient, cost-effective and environmentally-friendly process for making 2-(6-methoxy-2-naphthyl) propenoic acid is needed.

SUMMARY OF THE INVENTION

An efficient, cost-effective and environmentally-friendly process for making 2-(6-methoxy-2-naphthyl) propenoic acid ester, which can then easily be converted to 2-(6-methoxy-2 naphthyl) propenoic acid, and then from there to naproxen, using known techniques, has been discovered. Moreover, this process can be used to make other 2-aryl substituted propenoic acid esters, which in turn can be used to produce a wide variety of NSAIDs, including, but not limited to, ibuprofen, ketoprofen, flurbiprofen, fenaprofen, indoprofen, cicloprofen, carprofen, pirprofen, suprofen, and tiaprofenic acid.

For the production of NSAIDs, an aryl aldehyde, where the aryl group is a substituted or unsubstituted aromatic or heteroaromatic group, is reacted with an alkyldiazoacetate in the presence of a catalytic amount of fluoroboric acid or an iron Lewis acid to provide a 2-aryl-3-hydroxy-propenoic acid ester. The 2-aryl-3-hydroxy-propenoic acid ester is then reduced to provide a 2-aryl-propenoic acid ester, which can be converted to the desired NSAID by hydrolysis and hydrogenation.

Preferably, the substituted or unsubstituted aromatic or heteroaromatic group is (a) a phenyl group; (b) a phenyl group substituted with one, two or three substituents independently selected from alkyl halogen, cyano, carboxy, cycloalkyl, nitro, alkoxy, phenyl or substituted phenyl, alkylcarbonyl of one to ten carbon atoms, benzoyl or substituted benzoyl, 1-oxo-isoindolyl, phenoxy or substituted phenoxy, azoline or thienylcarbonyl; (c) a naphthyl group; (d) a naphthyl group substituted with one or more of the substituents from (b) above; (e) a fluorenyl group; (f) a carbazoyl group; (g) a carbazoyl group substituted with one or more of the substituents from (b) above; (h) a thienyl group; (i) a thienyl group substituted with one or more of the substituents from (b) above; (j) a pyrrolyl group; (k) a pyrrolyl group substituted with one or more of the substituents from (b) above; (l) a furyl group; and (m) a furyl group substituted with one or more of the substituents from (b) above.

DESCRIPTION OF THE PREFERRED EMBODIMENTS

The present invention relates to the synthesis of compounds of the formula:

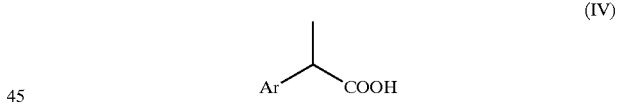

where Ar is a substituted or unsubstituted aromatic or heteroaromatic group. The term "aromatic" refers to a ring system having one or more aromatic rings including, but not limited to, phenyl, naphthyl, anthryl, phenanthryl, tetrahydronaphthyl, indanyl, indenyl and the like. Aromatic groups can be unsubstituted or substituted with one, two or three substituents independently selected from alkyl, halogen, haloalkyl, hydroxy, hydroxyalkyl, alkenyl, alkenyloxy, alkoxy, alkoxyalkoxy, alkoxycarbonyl, amino, alkylamino, alkylsulfonyl, dialkylamino, aminocarbonyl, aminocarbonylalkoxy, aryl, arylalkyl, arylalkoxy, aryloxy, cyano, nitro, carboxy, cycloalkyl, cycloalkylalkyl, carboxyalkoxy and phenyl.

The term "alkyl" as used herein refer to straight or branched chain containing from one to ten carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "alkoxy" as used herein refers to RO—, wherein R is a alkyl group, as defined above.

The term "cycloalkyl" as used herein refers to an aliphatic ring system having three to ten carbon atoms and one to three rings including, but not limited to, cyclopropyl, cyclopentyl, cyclohexyl, norbornyl, adamantyl and like.

The term "halogen" or "halo" refers to one of the electronegative elements of group VIIA of the periodic table, such as fluorine, chlorine, bromine, iodine and astatine.

The term "heteroaromatic" refers to any 5-, 6-, 7-membered aromatic ring containing one or more nitrogen, oxygen, or sulfur atoms, or any combination thereof. The term "heteroaromatic" also includes bicyclic groups in which any of the above heterocyclic rings is fused to a benzene ring or another heterocyclic ring (for example, indolyl, quinolyl, benzofuryl or benzothienyl and the like).

Heteroaromatics include, but are not limited to, pyrrolyl, pyrrolinyl, imidazolyl, pyridyl, indolyl, furyl, thienyl, isoindolyl.

Preferably, the substituted or unsubstituted aromatic or heteroaromatic group is (a) a phenyl group; (b) a phenyl group substituted with one, two or three substituents independently selected from alkyl, halogen, cyano, carboxy, cycloalkyl, nitro, alkoxy, phenyl or substituted phenyl, alkylcarbonyl of one to ten carbon atoms, benzoyl or substituted benzoyl, 1-oxo-isoindolyl, phenoxy or substituted phenoxy, azoline or thienylcarbonyl; (c) a naphthyl group; (d) a naphthyl group substituted with one or more of the substituents from (b) above; (e) a fluorenyl group; (f) a carbazoyl group; (g) a carbazoyl group substituted with one or more of the substiuents from (b) above; (h) a thienyl group; (i) a thienyl group substituted with one or more of the substituents from (b) above; (j) a pyrrolyl group; (k) a pyrrolyl group substituted with one or more of the substituents from (b) above; (l) a furyl group; and (m) a fturyl group substituted with one or more of the substituents from (b) above.

More preferably, the process of the present invention is used to produce NSAID compounds of formula (IV) above such as naproxen (Ar is 6-methoxy-2-naphthalenyl), ibuprofen (Ar isp-isobutylphenyl), ketoprofen (Ar is m-benzoylphenyl), flurbiprofen (Ar is 2-fluoro-4-biphenyl), fenaprofen (Ar is m-phenoxyphenyl), indoprofen (Ar is p-(1-oxo-2-isoindolinyl)-phenyl), cicloprofen (Ar is fluorenyl), carprofen (Ar is 6-chlorocarbazolyl), pirprofen (Ar is 3-chloro-4-(3-pyrrolin-1-yl)-phenyl), tiaprofenic acid (Ar is 5-benzoyl-2-thienyl), and suprofen (Ar is p-2-thienoyl-phenyl).

Most preferably, the process of the present invention is used to manufacture naproxen.

The compounds of formula (IV) are produced by reacting an aldehyde of the formula:

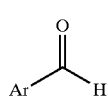

(I)

where Ar is as described above, with an alkyldiazoacetate of the formula N$_2$CHCOOR, where R is an alkyl group in the presence of catalytically effective amount of either a Bronsted acid or a Lewis acid, to produce a 2-aryl-3-hydroxy propenoic acid ester of the formula:

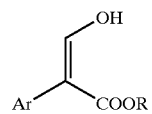

(II)

where Ar and R are as described above.

The term "Bronsted acid" refers any molecule or ion that can donate a hydrogen ion (H$^+$) to another molecule or ion by forming a bond with two electrons to form a second molecule or ion. Examples of suitable Bronsted acids that can be used include, but are not intended to be limited to, fluoroboric acid, perchloric acid, sulfuric acid, hydrohalic acid, nitric acid, triflic acid and phosphoric acid. The use of fluoroboric acid (HBF$_4$) is preferred. The Bronsted acid, if used, should generally be present in an amount from about 0.01 to about 1 molar equivalent per equivalent of compound (I), and is preferably present in an amount of from about 0.05 to about 0.1 molar equivalents per equivalent of compound (I).

The term "Lewis acid" refers to any molecule or ion that can combine with another molecule or ion by forming a bond with two electrons to form a second molecule or ion. Examples of suitable Lewis acids that can be used in the present invention include, but are not intended to be limited to, zinc chloride, tin chloride, aluminum chloride, boron trifluoride, and iron Lewis acids, such as [CpFe(CO)$_2$(THF)]$^+$. Use of [CpFe(CO)$_2$(THF)]$^+$ is preferred. If a Lewis acid is used, it should generally be present in an amount from about 0.01 to about 0.5 molar equivalents per equivalent of compound (I) and is preferably present in an amount of from about 0.01 to about 0.1 molar equivalents per equivalent of compound (I). The alkyldiazoacetate is preferably ethyldiazoacetate or methyldiazoacetate and should generally be present in an amount of from about one to about two molar equivalents per equivalent of compound (I).

The reaction is carried out at a temperature of from +40° C. to about –90° C., preferably at a temperature from about room temperature to about –78° C., in a solvent that is suitable for use with the above reactants. Any polar or nonpolar solvent or mixture of polar and nonpolar solvents can be used in the process of the present invention. Suitable solvents include, but are not limited to, pentane, hexane, ether, methylene chloride, cyclohexane, xylene, mesitylene, chlorobenzene, tetrahydrofuran, 1,4-dioxane, fluorobenzene and mixtures thereof. The use of methylene chloride is preferred.

The resulting compound of formula (II) above is then reduced in the presence of an alkyl amine where alkyl is as described above to produce a 2-aryl propenoic acid ester of the formula:

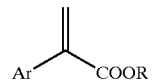

(III)

where Ar and R are as described above.

Suitable reducing agents for use in producing the compound of formula (II) above include, but are not limited to, NH$_3$ in Li, Na, or K; metal hydrides (including, but not limited to, NaH, LiH, BH$_3$, NaBH$_4$, LiAlH$_4$, LiBH$_4$, Zn(BH$_4$)$_2$, NaBH$_3$CN, LiHBEt$_3$, AlH$_3$, and Et$_3$SiH); H$_2$/Pd; H$_2$/Pt; and HCHO in acid or in base. A preferred reducing agent is BH$_3$ complexed with polar protic or aprotic solvents. The most preferred reducing agent is BH$_3$.THF. The reducing agent should be present in an amount from about 0.5 to about 3 molar equivalents per equivalent compound (II), with an amount of from about 1 to about 1.5 molar equivalents per equivalent of compound (II) being preferred. Any polar protic or aprotic solvent can be used in the process of the present invention. Suitable solvents include, but are not limited to, alcohol, ether, tetrahydrofuran ("THF"), 1,4-dioxane, and mixtures thereof. The use of THF is preferred.

The reaction should also proceed in the presence of an alkyl amine or an aryl amine, where alkyl and aryl are as described above. Of the amines, secondary amines are preferred for use in the present invention. The term "secondary amine" refers to dialkyl amine, alkylarylamine, diarylamine, or heterocyclic amines, where alkyl and aryl are as described above. The term "heterocyclic" as used herein refers to any 3- or 4-membered ring containing nitrogen atom or a 5-, 6-, or 7-membered ring containing one, two or three nitrogen atoms, or one nitrogen and one oxygen atom. Of the secondary amines, the use of pyrrolidine, piperidine or oxazoborolidine is preferred. The secondary amine should be present in an amount from about 0.01 to about 1 molar equivalent per equivalent of compound (II), with an amount of from about 0.05 to about 0.2 molar equivalents being preferred.

The resulting 2-aryl-propenioc acid ester compound of formula (III) can then be hydrolyzed to its corresponding 2-aryl-propenoic acid by known techniques using KOH, NaOH or Ba(OH)$_2$. That compound can then be converted to its corresponding 2-aryl-propanoic acid (an NSAID) of formula (IV) by known hydrogenation reactions, such H$_2$/Pd or H$_2$/Ni. The hydrolysis and hydrogenation steps may also be reversed, if desired. The 2-aryl-propenoic acid of formula (IV) can also be converted to one of its pharmaceutically acceptable salts by known techniques, if desired. In this manner, NSAIDs such as naproxen, ibuprofen, ketoprofen, flurbiprofen, indoprofen, carprofen, suprofen, fenaprofen, and their pharmaceutically acceptable salts can be made.

While the above process can be used to make a wide variety of NSAIDs, it is preferably used in the production of naproxen and its pharmaceutically acceptable salts, especially the sodium salt. To make naproxen, which has the formula:

(IX)

6-methoxynaphthyl aldehyde of the formula:

(V)

is used as the starting material, and is reacted with an alkyldiazoacetate (N$_2$CHCOOR) where R is alkyl as described above, to yield 2-(6-methoxy-2-naphthyl)-3-hydroxy propenoic acid ester, which has the formula:

(VI)

where R is as described above.

That compound is then preferably reduced with BH$_3$.THF in the presence of a secondary amine, preferably piperidine, pyrrolidine or oxazoborolidine, to yield 2-(6-methoxy-2-naphthyl)propenoic acid ester, which has the formula:

(VII)

where R is as described above.

The compound of formula (VII) can be converted to 2-(6-methoxy-2-naphthyl) propanoic acid, naproxen, by first hydrolyzing it to form 2-(6-methoxy-2-naphthyl) propenoic acid of the formula:

(VIII)

That compound is then reduced to naproxen by known catalytic asymmetric hydrogenation processes, using, for example a Ru-BINAP catalyst disclosed in U.S. Pat. No. 5,198,561, or a tol-BINAP catalyst disclosed in Ohta et al., J Org-Chem., 1987, 52, 3174. The resulting naproxen can be converted to one of its pharmaceutically acceptable salts by known techniques, if desired.

Example 1

Various 2-aryl-3-hydroxy-propenoic acid esters were prepared in accordance with the following procedure. 0.1 molar equivalents of [CpFe(CO)$_2$(THF)]$^+$ were dissolved in a solvent under nitrogen. One equivalent of an aryl aldehyde was added. The solution was cooled to 0° C. Ethyldiazoacetate (1.2 equivalents) was added drop-wise over a period of 6–7 hours. The reaction mixture was stirred for another 10–12 hours at 0° C. After the reaction was judged complete, the solvent was removed by rotary evaporation and the product was isolated by column chromatography (2–10% ether in pentane).

Example 1A 2-phenyl-3-hydroxy-propenoic acid ester in a yield of 70% was produced from benzaldehyde, according to the procedure of Example 1, where the solvent was methylene chloride.

Example 1B 2-(4-methylphenyl)-3-hydroxy-propenoic acid ester in a yield of 67% was produced from 4-methylbenzaldehyde, according to the procedure of Example 1, where the solvent was methylene chloride.

Example 1C 2-(4-methoxyphenyl)-3-hydroxy-propenoic acid ester in a yield of 60% was produced from 4-methoxybenzaldehyde, according to the procedure of Example 1, where the solvent was methylene chloride.

Example 1D 2-(2,4-dimethoxyphenyl)-3-hydroxy-propenoic acid ester in a yield of 80% was produced from 2,4-dimethoxybenzaldehyde, according to the procedure of Example 1, where the solvent was methylene chloride.

Example 1E 2-(4-chlorophenyl)-3-hydroxy-propenoic acid ester in a yield of 60% was produced from 4-chlorobenzaldehyde, according to the procedure of Example 1, where the solvent was methylene chloride.

Example 1F 2-(2-nitrophenyl)-3-hydroxy-propenoic acid ester in a yield of 65% was produced from 4-nitrobenzaldehyde, according to the procedure of Example 1, where the solvent was methylene chloride.

Example 1G 2-(6-methoxy-2-naphthyl)-3-hydroxy-propenoic acid ester in a yield of 80% was produced from 4-methoxy-2-naphthaldehyde, according to the procedure of Example 1, where the solvent was methylene chloride.

Example 2

Various 2-aryl-3-hydroxy-propenoic acid esters were prepared in accordance with the following procedure. 0.1 molar equivalents of $HBF_4$ acid catalyst were dissolved in a solvent under nitrogen. One equivalent of aryl aldehyde was added. The solution was cooled to 0° C. Ethyldiazoacetate (1.2 equivalents) was added drop-wise over a period of 6–7 hours. The reaction mixture was stirred for another 10–12 hours at 0° C. After the reaction was judged complete, the solvent was removed by rotary evaporation and the product was isolated by column chromatography (2–10% ether in pentane).

Example 2A 2-phenyl-3-hydroxy-propenoic acid ester in a yield of 55% was produced from benzaldehyde, according to the procedure of Example 1, where solvent was methylene chloride.

Example 2B 2-(4-methylphenyl)-3-hydroxy-propenoic acid ester in a yield of 60% was produced from 4-methylbenzaldehyde, according to the procedure of Example 1, where the solvent was methylene chloride.

Example 2C 2-(2-nitrophenyl)-3-hydroxy-propenoic acid ester in a yield of 73% was produced from 2-nitrobenzaldehyde, according to the procedure of Example 2, where the solvent was methylene chloride.

Example 2D 2-(5-methoxy-2-nitrophenyl)-3-hydroxy-propenoic acid ester in a yield of 68% was produced from 5-methoxy-2-nitrobenzaldehyde, according to the procedure of Example 2, where the solvent was methylene chloride.

Example 3

Various 2-aryl-3-hydroxy-propenoic acid esters were prepared in accordance with the following procedure. 0.1 molar equivalents of $HBF_4$ was dissolved in a solvent under nitrogen. One equivalent of aryl aldehyde was added. The solution was cooled to −78° C. Ethyldiazoacetate (1.2 equivalents) was added drop-wise over a period of 6–7 hours. The reaction mixture was stirred for another 10–12 hours at −78° C. After the reaction was judged complete, the solvent was removed by rotary evaporation and the product was isolated by column chromatography (2–10% ether in pentane).

Example 3A 2-phenyl-3-hydroxy-propenoic acid ester in a yield of 55% was produced from benzaldehyde, according to the procedure of Example 3, where solvent was methylene chloride.

Example 3B 2-(4-methylphenyl)-3-hydroxy-propenoic acid ester in a yield of 67% was produced from 4-methylbenzaldehyde, according to the procedure of Example 3, where the solvent was methylene chloride.

Example 3C 2-(5-methoxy-2-nitrophenyl)-3-hydroxy-propenoic acid ester in a yield of 67% was produced from 5-methoxy-2-nitrobenzaldehyde, according to the procedure of Example 3, where the solvent was methylene chloride.

Example 3D 2-(2,4-dimethoxy-2-nitrophenyl)-3-hydroxy-propenoic acid ester in a yield of 76% was produced from 2,4-dimethoxy-2-nitrobenzaldehyde, according to the procedure of Example 3, where the solvent was methylene chloride.

Example 3E 2-(4,5-methylenedioxy-2-nitrophenyl)-3-hydroxy-propenoic acid ester in a yield of 86% was produced from 4,5-methylenedioxy-2-nitrobenzaldehyde, according to the procedure of Example 3, where the solvent was methylene chloride.

Example 3F 2-(2-nitrophenyl)-3-hydroxy-propenoic acid ester in a yield of 55% was produced from 2-nitrobenzaldehyde, according to the procedure of Example 3, where the solvent was methylene chloride.

Example 3G 2-(6-methoxy-2-naphthyl)-3-hydroxy-propenoic acid ester in a yield of 60% was produced from 4-methoxy-2-naphthaldehyde, according to the procedure of Example 3, where the solvent was methylene chloride.

Example 4

Various 2-aryl-propenoic acid esters were prepared in accordance with the following procedure. One equivalent of a 2-aryl-3-hydroxy-propenoic acid ester produced according to the process of Examples 1 to 3 was dissolved in 25 ml of THF, and 0.1 molar equivalents of piperidine were added. The solution was cooled to 0° C. and BH₃.THF (1.5 equivalents) was added. The reaction mixture was stirred for 20 hours at 0° C. Water was added to quench the reaction and the organic compounds were extracted with ether (20 ml×3), dried over anhydrous sodium sulfate, and upon rotary evaporation provided the pure product.

Example 4A 2-phenyl-propenoic acid ester in a yield of 86% was produced from the product of Example 1A or 2A or 3A according to the procedure of Example 4.

Example 4B 2-(6-methoxy-2-naphthyl)-propenoic acid ester in a yield of 75% was produced from the product of Example 1G or Example 3G, according to the procedure of Example 4.

Example 5

Various 2-aryl-propenoic acid esters were prepared in accordance with the following procedure. One equivalent of a 2-aryl-3-hydroxy propenoic acid ester produced according to the process in Examples 1 to 3 was dissolved in 25 ml of THF and 0.05 equivalents of oxazoborolidine were added. The solution was cooled to 0° C. and BH₃.THF (1.5 equivalents) was added. The reaction mixture was stirred for 20 hours at 0° C. Water was added to quench the reaction and the organic compounds were extracted with ether (20 ml×3), dried over anhydrous sodium sulfate, and upon rotary evaporation provided the pure product.

Example 5A 2-phenyl-propenoic acid ester in a yield of 81% was produced from the product of Example 1A or 2A or 3A according to the procedure of Example 5.

Example 5B 2-(6-methoxy-2-naphthyl)-propenoic acid ester in a yield of 85% was produced of Example 1G or Example 3G, according to the procedure of Example 5.

I claim:
1. A method of producing a compound of the formula:

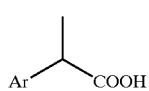
(IV)

and its pharmaceutically acceptable salts, wherein Ar is a substituted or unsubstituted aromatic or heteroaromatic group; comprising:
(1) reacting a compound of the formula:

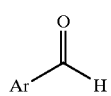
(I)

wherein Ar is as described above, with N₂CHCOOR, wherein R is alkyl, in the presence of a catalytic amount of a Bronsted acid or Lewis acid to form a compound of the formula:

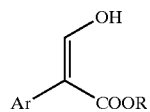
(II)

wherein Ar and R are as described above;
(2) reacting the compound of formula (II) with a reducing agent in the presence of an alkyl amine to form a compound of the formula:

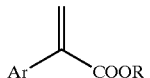
(III)

wherein Ar and R are as described above;
(3) hydrolyzing the compound of formula (III) to a compound of the formula:

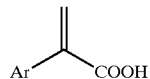
(X)

wherein Ar is as described above; and
(4) hydrogenating the compound of formula (X) to a compound of formula (IV) wherein Ar is as described above.

2. The method of claim 1 wherein Ar is selected from the group consisting of (a) a phenyl group; (b) a phenyl group substituted with one or more of alkyl, halogen, cycloalkyl, nitro, alkoxy, phenyl or substituted phenyl, alkylcarbonyl of one to ten carbon atoms, benzoyl or substituted benzoyl, 1-oxo-isoindolyl, phenoxy or substituted phenoxy, azoline or thienylcarbonyl; (c) a naphthyl group; (d) a naphthyl group substituted with one or more of the substituents from (b) above; (e) a fluorenyl group; (f) a carbazoyl group; (g) a carbazoyl group substituted with one or more of the substituents from (b) above; (h) a thienyl group; (i) a thienyl group substituted with one or more of the substituents from (b) above; (j) a pynoyl group; (k) a pyrroyl group substituted with one or more of the substituents from (b) above; (l) a furyl group; and (m) a furyl group substituted with one or more of the substituents from (b) above.

3. The method of claim 1 wherein Ar is selected from the group consisting of 6-methoxy-2-naphthalenyl, p-isobutylphenyl, m-benzoylphenyl, 2-fluoro-4-biphenyl, m-phenoxyphenyl, p-(1-oxo-2-isoindolinyl)-phenyl, fluorenyl, 6-chlorocarbazoyl, 3-chloro-4-(3-pyrrolin-1-yl)-phenyl, 5-benzoyl-2-thienyl, and p-2-thienoylphenyl.

4. The method of claim 3 wherein the reducing agent is BH₃.THF.

5. The method of claim 3 wherein the alkyl amine is a secondary amine.

6. The method of claim 3 wherein the secondary amine is selected from the group consisting of piperidine and oxazaborolidine and is present in an amount of from about 0.05 to 0.2 molar equivalents per equivalent of compound (II).

7. The method of claim 3 wherein the Bronsted acid is HBF₄.

8. The method of claim 3 wherein the Lewis acid is an iron Lewis acid.

9. The method of claim 8 wherein the iron Lewis acid is [CpFe(CO)₂(THF)]⁺.

10. A method of producing a compound of the formula:

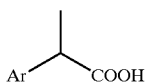
(IV)

and its pharmaceutically acceptable salts wherein Ar is a substituted or unsubstituted aromatic or heteroaromatic group, comprising reacting a compound of the formula:

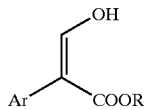
(II)

wherein Ar is as described above and R is alkyl with a reducing agent in the presence of alkyl amine to form a compound of the formula:

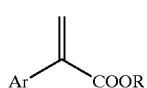
(III)

wherein Ar and R are as describe above;
hydrolyzing the compound of formula (XII) to a compound of the formula:

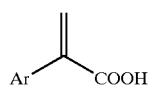
(X)

wherein Ar is as described above; and
hydrogenating the compound of formula (X) to a compound of formula (TV) wherein Ar is as described above.

11. The method of claim 10 wherein Ar is selected from the group consisting of (a) a phenyl group; (b) a phenyl group substituted with one or more of alkyl, halogen, cycloalkyl, nitro, alkoxy, phenyl or substituted phenyl, alkylcarbonyl of one to ten carbon atoms, benzoyl or substituted benzoyl, 1-oxo-isoindolyl, phenoxy or substituted phenoxy, azoline or thienylcarbonyl; (c) a naphthyl group; (d) a naphthyl group substituted with one or more of the substituents from (b) above; (e) a fluorenyl group; (f) a carbazoyl group; (g) a carbazoyl group substituted with one or more of the substituents from (b) above; (h) a thienyl group; (i) a thienyl group substituted with one or more of the substituents from (b) above; (j) a pyrrolyl group; (k) a pyrrolyl group substituted with one or more of the substituents from (b) above; (i) a furyl group; and (m) a furyl group substituted with one or more of the substituents from (b) above.

12. The method of claim 10, wherein Ar is selected from the group consisting of 6-methoxy-2-naphthalenyl, p-isobutylphenyl, m-benzoylphenyl, 2-fluoro-4-biphenyl, m-phenoxyphenyl, p-(1-oxo-2-isoindolinyl)-phenyl, fluorenyl, 6-chlorocarbazoyl, 3-chloro-4-(3-pyrrolin-1-yl)-phenyl, 5-benzoyl-2-thienyl, and p-2-thienoylphenyl.

13. The method of claim 12 wherein the reducing agent is $BH_3.THF$.

14. The method of claim 12 wherein the alkyl amine is a secondary amine.

15. The method of claim 12 wherein the secondary amine is selected from the group consisting of piperidine and oxazaborolidine and is present in an amount of from about 0.05 to about 0.2 molar equivalents per equivalent of compound (II).

16. The method of claim 1 wherein the Bronsted acid or Lewis acid is $HBF_4$.

17. The method of claim 16 wherein Ar is selected from the group consisting of (a) a phenyl group; (b) a phenyl group substituted with one or more of alkyl, halogen, cycloalkyl, nitro, alkoxy, phenyl or substituted phenyl, alkylcarbonyl of one to ten carbon atoms, benzoyl or substituted benzoyl, 1-oxo-isoindolyl, phenoxy or substituted phenoxy, azoline or thienylcarbonyl; (c) a naphthyl group; (d) a naphthyl group substituted with one or more of the substituents from (b) above; (e) a fluorenyl group; (f) a carbazoyl group; (g) a carbazoyl group substituted with one or more of the substituents from (b) above; (h) a thienyl group; (i) a thienyl group substituted with one or more of the substituents from (b) above; (j) a pyrrolyl group; (k) a pyrrolyl group substituted with one or more of the substituents from (b) above; (l) a furyl group; and (m) a furyl group substituted with one or more of the substituents from (b) above.

18. The method of claim 16, wherein Ar is selected from the group consisting of 6-methoxy-2-naphthalenyl, p-isobutylphenyl, m-benzoylphenyl, 2-fluoro-4-biphenyl, m-phenoxyphenyl, p-(1-oxo-2-isoindolinyl)-phenyl, fluorenyl, 6-chlorocarbazoyl, 3-chloro-4-(3-pyrrolin-1-yl)-phenyl, 5-benzoyl-2-thienyl, and p-2-thienoylphenyl.

19. A method of producing naproxen and its pharmaceutically acceptable salts comprising: (I) reacting an aldehyde of the formula:

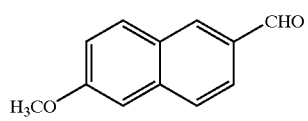
(V)

with $N_2CHOOR$, wherein R is alkyl, in the presence of a Bronsted acid or a Lewis acid to produce a compound of the formula:

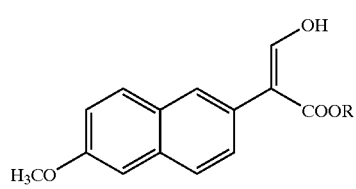
(VI)

wherein R is as described above;
(2) reacting the compound of formula (VI) with a reducing agent in the presence of an alkyl amine to produce a compound of the formula:

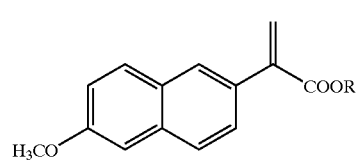
(VII)

wherein R is as described above;
(3) hydrolyzing the compound of formula (VII) to a compound of the formula:

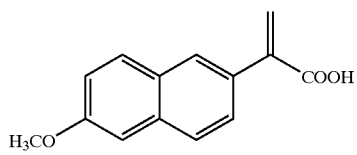

and (4) hydrogenating the compound of formula (XI) to naproxen or its pharmaceutically acceptable salts.

20. The method of claim 19 wherein the reducing agent is $BH_3 \cdot THF$.

21. The method of claim 19 wherein the alkyl amine is a secondary amine.

22. The method of claim 19 wherein the secondary amine is chosen from a group consisting of piperidine and oxazoboralidine and is present in an amount of from about 0.05 to about 0.2 molar equivalents per equivalent of compound (IV).

23. The method of claim 19 wherein the Bronsted acid is $HBF_4$.

24. The method of claim 19 wherein the Lewis acid is an iron Lewis acid.

25. The method of claim 24 wherein the iron Lewis acid is $[CpFe(CO)_2(THF)]^+$.

26. A method of producing naproxen and its pharmaceutically acceptable salts comprising reacting a compound of the formula:

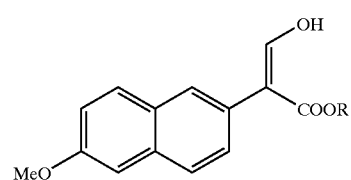

wherein R is alkyl with a reducing agent in the presence of an alkyl amine to produce a compound of the formula:

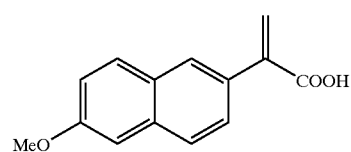

wherein R is as described above,
hydrolyzing the compound of formula (VII) to a compound of the formula:

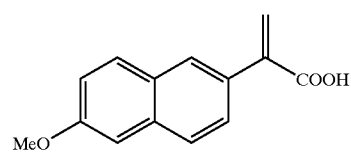

and hydrogenating the compound of formula (XI) to naproxen or its pharmaceutically acceptable salts.

27. The method of claim 26 wherein the reducing agent is $BH_3 \cdot THF$.

28. The method of claim 26 wherein the alkyl amine is a secondary amine.

29. The method of claim 26 wherein the secondary amine is selected from a group consisting of piperidine and oxazoboralidine and is present in an amount of from about 0.05 to about 0.2 molar equivalents per equivalent of compound (VI).

30. The method of claim 19 wherein the Bronsted acid or Lewis acid is $HBF_4$.

31. A method of producing a compound of the formula:

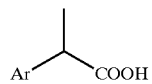

and its pharmaceutically acceptable salts, wherein Ar is a substituted or unsubstituted aromatic or heteroaromatic group; comprising:

(1) reacting a compound of the formula;

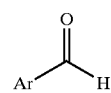

wherein Ar is as described above, with $N_2CHCOOR$, wherein R is alkyl, in the presence of a catalytic amount of a Bronsted acid or Lewis acid to form a compound of the formula:

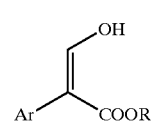

wherein Ar and R are as described above;

(2) reacting the compound of formula (II) with a reducing agent in the presence of an alkyl amine to form a compound of the formula:

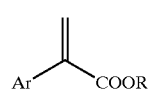

wherein Ar and R are as described above, (3) hydrogenating the compound of formula (III) to a compound of the formula

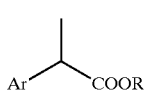

wherein Ar and R are as described above; and (4) hydrolyzing the compound of formula (XII) to a Compound of formula (IV) wherein Ar is as described above.

32. A method of producing a compound of the formula:

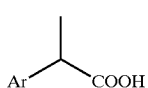
(IV)

and its pharmaceutically acceptable salts wherein Ar is a substituted or unsubstituted aromatic or heteroaromatic group, comprising reacting a compound of the formula:

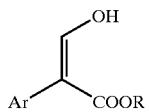
(II)

wherein Ar is as described above and R is alkyl with a reducing agent in the presence of alkyl amine to form a compound of the formula:

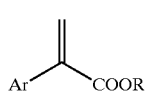
(III)

wherein Ar and R are as describe above;
hydrogenating the compound of formula (III) to a compound of the formula:

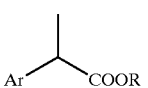
(XII)

wherein Ar is as described above; and
hydrolyzing the compound of formula (XI) to a compound of formula (IV) wherein Ar is as described above.

33. The method of claim 31 wherein the Bronsted acid or Lewis acid is $HBF_4$.

34. A method of producing naproxen and its pharmaceutically acceptable salts comprising: (1) reacting an aldehyde of the formula:

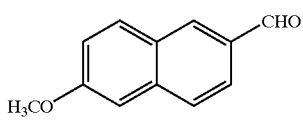
(V)

with $N_2CHCOOR$ wherein R is alkyl, in the presence of a Bronsted acid or a Lewis acid to produce a compound of the formula:

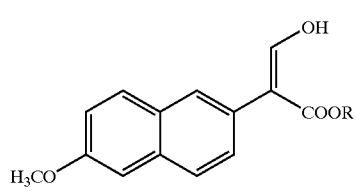
(VI)

wherein R is as described above;
(2) reacting the compound of formula (VI) with a reducing agent in the presence of an alkyl amine to produce a compound of the formula:

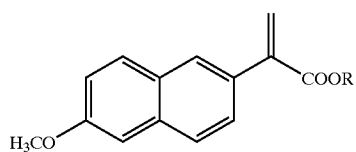
(VII)

wherein R is as described above;
(3) hydrogenating the compound of formula (VII) to a compound of the formula:

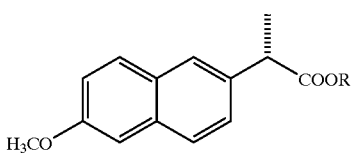
(XIII)

and
(4) hydrolyzing the Compound of formula (XIII) to naproxen or its pharmaceutically acceptable salts.

35. A method of producing naproxen and its pharmaceutically acceptable salts comprising reacting a compound of the formula:

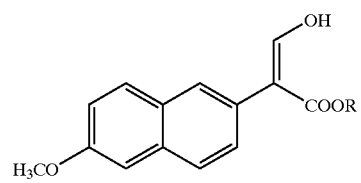
(VI)

wherein R is alkyl with a reducing agent in the presence of an alkyl amine to produce a compound of the formula:

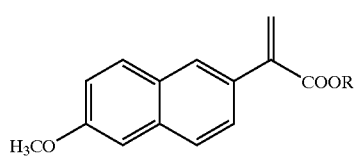
(VII)

wherein R is as described above;
hydrogenating the compound of formula (VII) to a compound of the formula:

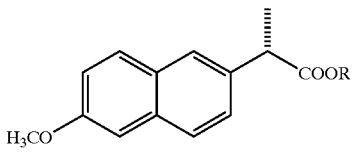
(XIII)

and hydrogenating the compound of formula (XI) to naproxen or its pharmaceutically acceptable salts.

36. The method of claim 34 wherein the Bronsted acid or Lewis acid is $HBF_4$.

* * * * *